United States Patent
Kawanishi et al.

(10) Patent No.: US 6,541,956 B2
(45) Date of Patent: Apr. 1, 2003

(54) CARRIER IDENTIFICATION SYSTEM, CARRIER IDENTIFICATION METHOD AND STORAGE MEDIA

(75) Inventors: Yuuji Kawanishi, Tokyo (JP); Yoshiaki Uchino, Tokyo (JP)

(73) Assignee: Ando Electric Co., Ltd., Tokyo (JP)

( * ) Notice: Subject to any disclaimer, the term of this patent is extended or adjusted under 35 U.S.C. 154(b) by 14 days.

(21) Appl. No.: 09/755,321

(22) Filed: Jan. 5, 2001

(65) Prior Publication Data

US 2001/0010462 A1 Aug. 2, 2001

(30) Foreign Application Priority Data

Jan. 28, 2000 (JP) .......................... 2000-020487

(51) Int. Cl.⁷ .............................................. G01R 31/02
(52) U.S. Cl. ................................................ 324/158.1
(58) Field of Search ........................... 324/73.1, 158.1, 324/763, 765, 759; 714/736; 702/122; 356/601, 610, 614, 399, 400

(56) References Cited

U.S. PATENT DOCUMENTS

| | | | | |
|---|---|---|---|---|
| 4,380,070 A | * | 4/1983 | Steiner | 714/736 |
| 5,289,113 A | * | 2/1994 | Meaney et al. | 324/73.1 |
| 5,642,307 A | * | 6/1997 | Jernigan | 365/103 |
| 5,832,419 A | * | 11/1998 | Voshell et al. | 702/122 |

FOREIGN PATENT DOCUMENTS

| | | |
|---|---|---|
| JP | 10-377095 | 12/1998 |

* cited by examiner

*Primary Examiner*—Vinh P. Nguyen
(74) *Attorney, Agent, or Firm*—Flynn, Thiel, Boutell & Tanis, P.C.

(57) ABSTRACT

In a horizontal carriage type auto handler, it is possible to identify a carrier efficiently without stopping the carrier when reading the carrier identification information provided in the carrier for transferring a device and to reduce the number of sensors for reading identification information. A plurality of timing holes and data holes are provided in the carrier as identification information. The carrier is detected when a timing hole detection sensor and a data hole detection sensor detect the timing holes and the data holes.

14 Claims, 3 Drawing Sheets

CARRIER IDENTIFICATION SYSTEM, CARRIER IDENTIFICATION METHOD AND STORAGE MEDIA

BACKGROUND OF THE INVENTION

1. Field of the Invention

The present invention relates to a carrier identification system for transferring semiconductor devices, and so forth, in an auto handler, a carrier identification method, and storage media.

2. Related Art

In an IC testing system for measuring electric properties of semiconductor devices such as an IC (integrated circuit), and so forth, use is made of an auto handler for transferring devices as objects for measurement. Semiconductor devices as objects for testing are mounted in a carrier, and selected by the auto handler.

In such a case, a plurality of carriers are simultaneously circulated inside the auto handler in order to improve efficiency, thereby selecting ICs.

Further, since the form of the carriers varies depending on a type of the semiconductor devices as the objects for testing, a controller of the auto handler needs to identify types of the semiconductor devices to be tested.

It is further required that, for example, nine units of the carriers are circulated inside the auto handler, and the respective carriers are assigned a serial number so as to be able to monitor all the time where the respective carriers are located inside the auto handler.

Accordingly, with a conventional auto handler, the respective carriers are assigned a bar code for carrier identification in order to identify a type of a semiconductor device mounted in the respective carriers, and the serial number of the respective carriers. A bar code reader reads the bar code assigned to the respective carriers, and identify the type of the semiconductor device mounted in the respective carriers, and the serial number of the respective carriers, on the basis of the bar code as read.

The above-described method is disclosed by the applicant of the present invention in, for example, Japanese Patent Application No. H 10-377095.

Further, there is available another method of identifying a type of semiconductor devices whereby a plurality of holes for identification are formed on a carrier. With this method, a plurality of sensors installed so as to correspond to the respective holes for identification read the holes for identification, provided in the carrier, and identify the type of semiconductor devices mounted in the carrier depending on a state of the holes, as read.

However, with the former method as described, the carrier needs to be stopped every time there is a need of reading data for carrier identification, and it has also been required that a location for stopping the carrier be in full agreement with that of a sensor for reading.

Meanwhile, with the latter method as described, whereby the holes for identification are formed in the carrier, it has been required that as many sensors for reading out as the holes for identification be installed.

SUMMARY OF THE INVENTION

Thus, problems to be solved by the invention are to eliminate a need of stopping carriers for transferring devices in order to read the data for carrier identification, and to be able to do with less numbers of the sensors for reading the data for carrier identification.

To solve the problems as described above, a carrier identification system according the first aspect of the invention, comprises a carrier (for example, a carrier 1 in FIG. 1) for mounting and transferring a plurality of devices to be tested (hereinafter referred to as DUTs), having identification information thereof, reading means (for example, a timing hole detection sensor 5 and a data hole detection sensor 6, in FIG. 1) for reading the identification information of the carrier, and identification means (for example, a device type identifying circuit 9 in FIG. 1) for identifying the carrier on the basis of the identification information as read by the reading means, wherein the carrier is provided with a plurality of timing holes (for example, timing holes 3 in FIG. 1) arranged in parallel with a direction of carrier transfer, and a plurality of data holes (for example, data holes 4 in FIG. 1) arranged in parallel with the direction of the carrier transfer, corresponding to arrangement locations of the plurality of the timing holes, and the reading means is provided with timing detection means (for example, timing hole detection sensor 5 in FIG. 1) disposed so as to correspond to the arrangement locations of the plurality of the timing holes, for detecting the plurality of the timing holes in conjunction with the carrier transfer, and data detection means (for example, data hole detection sensor 6 in FIG. 1) disposed so as to correspond to arrangement locations of the plurality of the data holes, for detecting the plurality of the data holes in conjunction with detection of the plurality of the timing holes by the timing detection means.

Further, a carrier identification method according to the third aspect of the invention comprises a transfer step of transferring a plurality of DUTs by use of a carrier with the plurality of the devices mounted therein, a reading step for reading identification information provided in the carrier, and an identification step of identifying the carrier on the basis of the identification information as read, said reading step including a timing detection step of detecting a plurality of timing holes arranged on the carrier, in parallel with a direction of carrier transfer, in conjunction with the carrier transfer, and a data detection step of detecting a plurality of data holes arranged on the carrier, in parallel with the direction of the carrier transfer, in conjunction with the timing detection step.

Therefore, according to the first and third aspects of the invention, the plurality of the timing holes and the data holes, disposed as the identification display in the carrier with the devices mounted therein, can be read one after another by the timing hole detection sensor and the data hole detection sensor, respectively, while the carrier is being transferred. As a result, it is possible to eliminate a need of stopping the carrier every time the identification display is read.

Further, as the sensors for reading the identification holes or markers on the carrier, only two kinds of sensors, that is, the timing hole detection sensor and the data hole detection sensor, are sufficient, and the number of the timing holes and the data holes can be increased or decreased with ease so as to correspond to the number of types of the carriers to be identified.

The invention according to the second aspect of the invention is a carrier identification system in the first aspect of the invention, wherein the timing detection means detect the plurality of the timing holes by transmission or shutoff of light (passage through the holes), the data detection means detect whether or not there exist the plurality of the data holes by transmission or shutoff of light, and the identification means generate a given code or data row according to whether or not there exist the plurality of the data holes as detected, thereby identifying the carrier on the basis of the data row as generated. The code row is defined as the output of the row of data holes and is a specific pattern depending on the type of carrier.

The invention according to the fourth aspect of the invention is a carrier identification method in the third aspect of the invention, wherein the timing detection step detects the plurality of the timing holes by transmission or shutoff of light, the data detection step detects whether or not there exist the plurality of the data holes by transmission or shutoff of light, and the identification step generates a given code row, corresponding to each data hole row, according to whether or not there exist the plurality of the data holes as detected, thereby identifying the carrier on the basis of the data hole row as generated or sensed.

Therefore, according to the second, fourth and sixth aspects of the invention, a state of the respective timing holes as well as the respective data holes as identification information can be detected by two kinds of states, that is, transmission and shutoff of light. By outputting and extracting such states as detected as digital signals, it is possible to set data rows wherein "1" and "0" are arranged. The DUTs can be identified by use of the data rows as the carrier identification information as DUTs known to be placed in the specific carrier.

PREFERRED EMBODIMENT OF THE INVENTION

An embodiment of the invention is described in detail hereinafter with reference to the accompanying drawings. First, the constitution thereof is described as follows.

Figure 1:
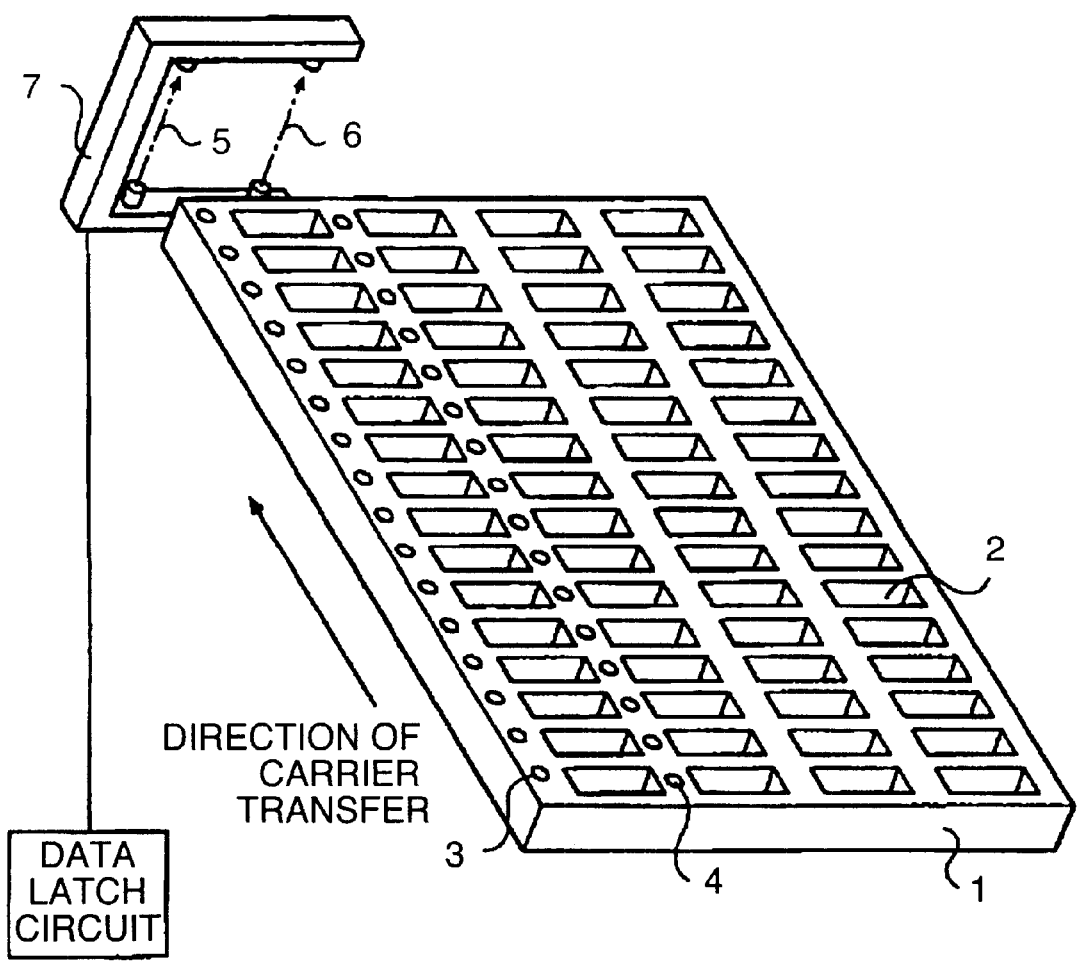
FIG. 1 is a perspective view showing an embodiment of a carrier identification system according to the invention.

FIG. 1 is a perspective view showing an embodiment of a carrier identification system according to the invention, made up of a carrier 1, a timing hole detection sensor 5, a data hole detection sensor 6, and a data latch circuit 8.

On the surface of the carrier 1, there are formed a plurality of cavities for mounting semiconductor devices as objects for testing, amounting to 64 in number, arrayed in rows and columns (16 rows×4 columns). Further, the carrier 1 is provided with timing holes 3 and data holes 4, which are formed in numbers corresponding to the number of the rows, as through-holes arranged in a transfer direction of the carrier 1, and which are defined on the side of the opposite short sides of the respective cavities 2, respectively, in such a way as to correspond to the respective locations of the cavities 2 lined up in the direction of columns of the carrier 1.

The timing hole detection sensor 5, and the data hole detection sensor 6, made up of a light emitting device in combination with an optical receiver, respectively, are installed on opposed faces on the side of the upper side and on the side of the lower side of a fitting member 7 in a form substantially resembling the letter U, respectively, and at a spacing identical to that provided between the respective timing holes 3 and the respective data holes 4. Further, the timing hole detection sensor 5 and the data hole detection sensor 6 detect a state of light being shut off from or transmitted through the timing holes 3, and the data holes 4, respectively, of the carrier 1 which is being transferred, Further, the timing hole detection sensor 5 and the data hole detection sensor 6 output a timing signal and a data signal, respectively, for expressing a detection condition of the timing holes 3 and the data holes 4, respectively, to be sent out to the data latch circuit 8.

Figure 3:
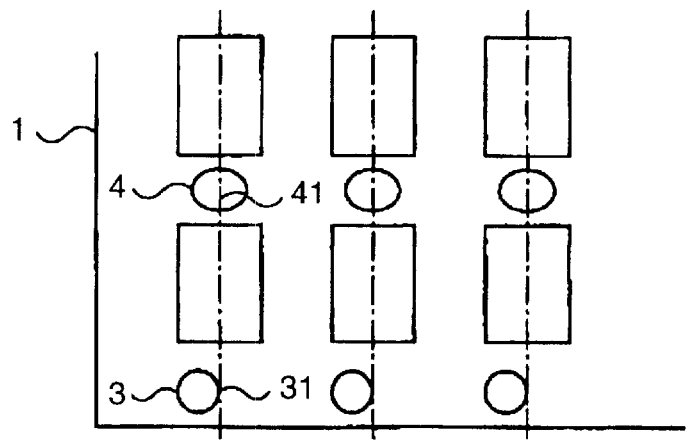
FIGS. 3(A), 3(B) and 3(C) show a partially enlarged view of a carrier 1 and a view indicating a relationship between the carrier and signals outputted by the sensors.
Figure 3:
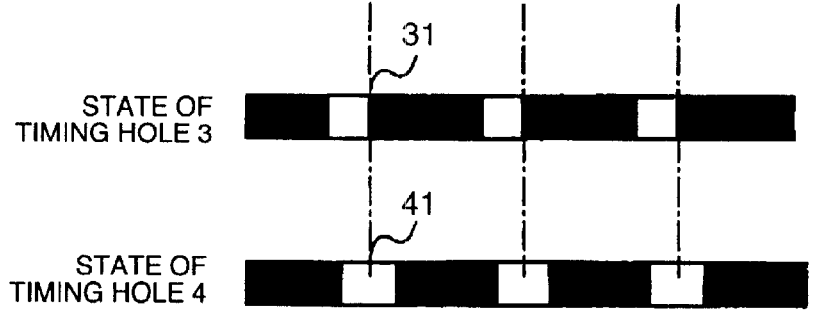
Figure 3:
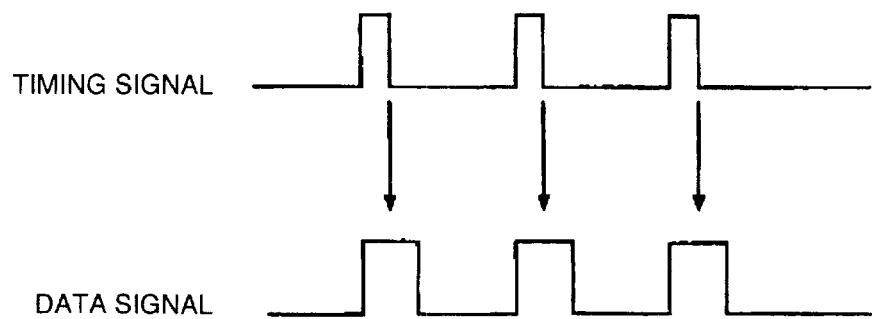

FIG. 3(A) is a partially enlarged plan view of the carrier 1, FIG. 3(B) a sectional view of the timing holes 3 and data holes 4, formed as through-holes in the carrier 1, and FIG. 3(C) shows the timing signal and the data signal as outputted by the timing hole detection sensor 5 and the data hole detection sensor 6, respectively.

The data holes 4 are formed so as to correspond to the timing holes 3, respectively, and as shown in FIG. 3(A), both the holes are configured such that a straight line interconnecting the center 41 of the respective data holes 4 and an edge 31 of the respective timing holes 3 is rendered perpendicular to the transfer direction of the carrier 1.

Further, as shown in FIG. 3(B), light is transmitted through a region (shown in white) where the respective timing holes 3 are formed, and shut off from all other regions (shown in black).

The timing hole detection sensor 5 and the data hole detection sensor 6 detect a state of light being shut off from or transmitted through the timing holes 3, and the data holes 4 of the carrier 1 being transferred, respectively. That is, as shown in FIG. 3(C), the timing hole detection sensor 5 and the data hole detection sensor 6 output the timing signal and the data signal as digital signals, respectively.

Further, as shown in the figure, the timing signal and the data signal undergo a change at an edge of the respective timing holes 3 and an edge of the respective data holes 4, respectively, that is, on the boundary face between the region in black and the region in white, turning to a low level when light is shut off therefrom, and turning to a high level when light is transmitted therethrough.

Then, upon the timing hole detection sensor 5 detecting the edge 21 of the respective timing holes 3, that is, upon detecting that a state of light relative to the respective timing holes 3 has undergone a change from a transmission state to a shutoff state (that is, change from a high level to a low level), the timing signal is extracted by the data latch circuit 8.

Thus, every time the respective timing holes 3 pass through a position of the timing hole detection sensor 5, the timing signal is extracted by the data latch circuit 8, and subsequently, the data signal outputted from the data hole detection sensor 6 is extracted. It is possible to set data rows of 16 bits in length, one bit expressing whether or not there exist the respective data holes 4, in numbers identical to the number of the timing holes 3 for every carrier. Types of the devices as the objects for testing are expressed by the data rows.

More specifically, in order to cause the data rows of 16 bits in length wherein "1" and "0" are arranged to correspond to the types of the respective DUTs mounted in the carrier 1 by detecting whether or not there exist each of 16 pieces of the data holes 4, the respective data holes 4 are formed at positions corresponding to "1" within the respective data rows of 16 bits, for expressing the types of the DUTs, but are not formed at other positions corresponding to "0". However, as for the timing holes 3, all of 16 pieces thereof are formed, and are used as a guide function for providing timing for extraction of the data signal.

Accordingly, 65536 (=$2^{16}$) types of carriers containing DUTs can be identified by making use of the data holes 4.

Figure 2:
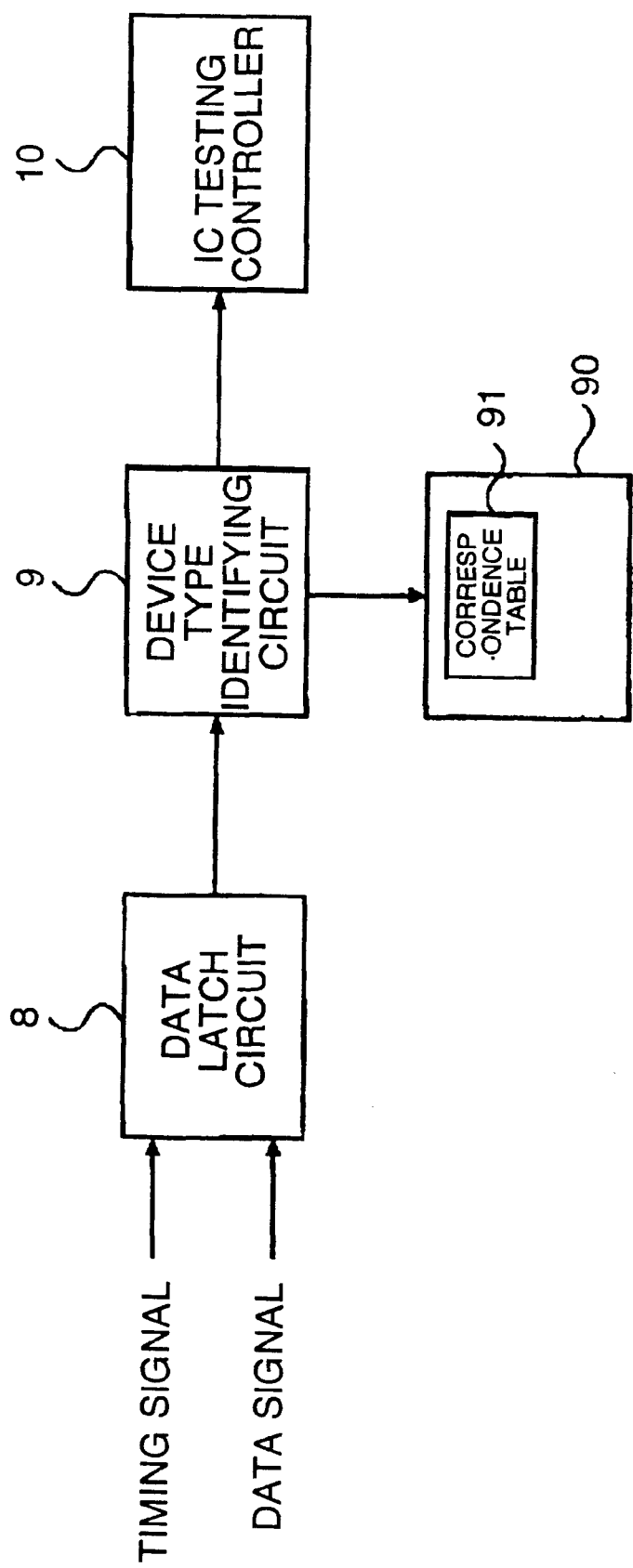
FIG. 2 is a view showing flow of signals detected by sensors.

As shown in FIG. 2, the timing signal and the data signal are inputted from the timing hole detection sensor 5 and the data hole detection sensor 6, respectively, to the data latch circuit 8. At a time when the timing signal as inputted undergoes a change from a high level to a low level, the data latch circuit 8 extracts the data signal, and latches the data signal of 16 bits in length, and inputs the same to a device type identifying circuit 9.

The device type identifying circuit 9 refers to a correspondence table 91 stored in storage media 90. On the basis of the data signal of 16 bits in length, input from the data latch circuit 8, the identifying circuit 9 identifies the carrier and thus the type of DUTs mounted in the carrier 1, and outputs the type as identified to a IC testing controller 10.

The correspondence table 91 stores a plurality of the data rows of 16 bits in length in such a way as to identify carriers and the corresponding respective types of DUTs. The table 91 is stored in the storage media 90 of the device type identifying circuit 9.

The IC testing controller 10 checks whether or not the types of the DUTs as inputted from the device type identifying circuit 9 is in agreement with types of devices as the objects of a test now under way. In case that there is no agreement, a step for control such as stopping the test now under way is taken.

Now, operation is described hereinafter.

As shown in FIG. 1, the carrier 1 with a semiconductor device as the object for IC testing, mounted in the plurality of the cavities 2 thereof, respectively, is transferred and passed between the upper side part, and the lower side part of the fitting member 7 with the timing hole detection sensor 5 and the data hole detection sensor 6, attached thereto.

The timing hole detection sensor 5 detects a state of light in relation to the respective timing holes 3 upon the optical receiver receiving light outputted by the light emitting device. Upon the carrier 1 passing the timing hole detection sensor 5, light outputted by the light emitting device is shut off, however, upon the respective timing holes 3 passing the timing hole detection sensor 5, light is not shut off by the respective timing holes 3, and is transmitted therethrough. The timing hole detection sensor 5 outputs such a state of light as the timing signal shown in FIG. 3(C) to the data latch circuit 8.

Similarly to the case of the timing hole detection sensor 5, the data hole detection sensor 6 also detects a state of the respective data holes 4 through shutoff and transmission of the light outputted by the light emitting device. Then, a state of the light as detected is outputted as the data signal shown in FIG. 3(C) to the data latch circuit 8.

Upon receiving the timing signal and the data signal as shown in FIG. 3(C) from the timing hole detection sensor 5 and the data hole detection sensor 6, respectively, the data latch circuit 8 extracts the data signal inputted according to a change in a state of the timing signal inputted.

More specifically, at a time when the timing hole detection sensor 5 detects a change in a state of the light from transmission to shutoff, the data signal is extracted. It means that, in FIG. 3(A), upon the timing hole detection sensor 5 passing the edge 31 of the respective timing holes 3, a state of the center 41 of the respective data holes 4 is extracted.

Further, every time the respective timing holes 3 pass the position of the timing hole detection sensor 5 of the fitting member 7 following transfer of the carrier 1, the data latch circuit 8 extracts the data signals one after another, corresponding to states of the respective data holes 4 passing the position of the data hole detection sensor 6.

After latching the data signals corresponding to 16 bits as extracted following transfer of the carrier 1, the data latch circuit 8 outputs the data rows of 16 bits in length to the device type identifying circuit 9.

The device type identifying circuit 9 refers to the correspondence table 91 stored in the storage media 90 on the basis of arrangement of "0" and "1" as set in the respective data signals of 16 bits in length, input from the data latch circuit 8, thereby identifying the carrier and the corresponding type of DUTs mounted in the carrier 1.

Upon identification of the type of the respective devices, the device type identifying circuit 9 outputs the types as identified to the IC testing controller 10, and clears the data signals inputted thereto.

Thereafter, the IC testing controller 10 performs control of operation while identifying types of the devices on the basis of the types inputted from the device type identifying circuit 9 every time the carrier 1 is transferred.

As described hereinbefore, in order to obtain identification information for identifying devices mounted in the carrier 1 for mounting the devices as objects for testing, the plurality of the timing holes 3 and the data holes 4 are provided. By detecting the state of the timing holes 3 as well as the data holes 4 by the agency of the optical sensors, the identification information can be read while the carrier 1 is being transferred.

Accordingly, since there is no need of stopping the carrier 1 when reading the identification information, delay in operation of the auto handler can be prevented.

Further, as the timing hole detection sensor and the data hole detection sensor for reading identification data can be made up of the light emitting device and the optical receiver, addition of the sensors, and addition of the timing holes as well as data holes, corresponding to an increase in the number of types to be identified, can be implemented with ease.

According to the first, third and fifth aspects of the invention, the plurality of the timing holes and the data holes, disposed as the identification holes or markers in the carrier with the devices mounted therein, can be read one after another by the timing hole detection sensor and the data hole detection sensor, respectively, while the carrier is being transferred. As a result, it is possible to eliminate stopping of the carrier every time the identification markers are read.

Further, as the sensors for reading the identification markers, only two kinds of sensors, that is, the timing hole detection sensor and the data hole detection sensor, are required, and the number of the timing holes and the data holes can be increased or decreased with ease so as to correspond to the number of types of the carriers to be identified.

According the second, fourth and sixth aspects of the invention, a state of the respective timing holes as well as the respective data holes as the identification information can be detected in two kinds of states, that is, transmission and shutoff of light, in addition of the effect of the first, third and fifth aspects of the invention. By outputting and extracting such states as detected in the form of digital signals, it is possible to set the data rows wherein "1" and "0" are arranged. The DUTs, for example, can be identified by use of the data rows as the identification information.

What is claimed is:

1. A carrier identification method comprising:
   a transfer step of transferring a plurality of devices under test by use of a carrier with the plurality of the devices mounted therein;
   a reading step for reading identification information provided in the carrier; and
   an identification step of identifying the carrier on the basis of the identification information as read, said reading step including:
      a timing detection step of detecting a plurality of timing holes arranged on the carrier, in parallel with a direction of carrier transfer, in conjunction with the carrier transfer, and
      a data detection step of detecting a plurality of data holes arranged on the carrier, in parallel with the direction of the carrier transfer, in conjunction with the timing detection step.

2. The carrier identification method according to claim 1, wherein the timing detection step detects the plurality of the timing holes by transmission or shutoff of light, the data detection step detects whether or not there exist the plurality of the data holes by transmission or shutoff of light, and the identification step generates a given data row according to whether or not there exist the plurality of the data holes as detected, thereby identifying the carrier on the basis of the data row as generated.

3. A carrier identification system applied to an autohandler comprising:
   a plurality of carriers for implementing and transferring a plurality of different types of devices under test, each device under test required to be identified, and each carrier provided with timing hole rows and data hole rows at given positions and serving as means for identifying each device under test implemented thereon;
   timing detection means for detecting timing hole rows implemented on the carrier while the carrier is transferred, and data detection means for detecting the data hole rows while the carrier is transferred, said timing detection means and said data detection means serving as reading means;
   wherein the timing hole rows provided in each carrier are bored in a preselected interval along a direction of the carrier and arranged serially and have the same size, and the data hole rows provided in each carrier are arranged in parallel with the timing hole rows at the same interval as the interval of timing holes of the timing hole rows and the data holes have a maximum number equal to or less than the number of the timing holes;
   each of the data holes of each of the data hole rows constitutes part of a given code row having a pattern showing whether or not there exists a data hole by selecting whether or not there exists a data hole from the leading position of the timing holes in a predetermined order, said data hole row being implemented on each carrier in advance for identifying the carrier and serving as identification information; and
   each timing hole constituting the timing hole rows provides timing for identifying whether or not there exists a corresponding data hole in the data hole rows while the carrier is being transferred.

4. The carrier identification system according to claim 3, wherein the timing detection means detect the plurality of the timing holes by transmission or shutoff of light, the data detection means detect whether or not there exist the plurality of the data holes by transmission or shutoff of light, and the identification means generates a given code row according to whether or not there exist the plurality of the data holes as detected, thereby identifying the carrier on the basis of the code row as generated.

5. A carrier identification system for a carrier transferring semiconductor devices comprising:
   a plurality of carriers for receiving and transferring a plurality of different types of devices under test, each said carrier being provided with timing through holes defining a timing hole row and data through holes defining a data hole row, said data hole row being utilized to identify said carrier, said timing through holes being spaced serially along the direction of travel of the carrier to form the timing hole row and said data hole row arranged in parallel with the timing hole row for each of said carriers so that the data through holes are paired with corresponding ones of the timing through holes, and wherein said data through holes do not exist in every instance for the corresponding said timing through hole;
   a timing detector for detecting the presence of the timing through holes along one of the timing hole rows while one of said carriers is moving to transfer devices under test placed thereon;
   a data detector for detecting the presence or absence of the respective data through holes;
   a circuit for receiving outputs from the timing detector and the data detector, the circuit storing data signals corresponding to the detected data through holes corresponding to the respective timing through holes; and
   a storage media for comparing the detected data signals to a plurality of different stored data signals.

6. The carrier identification system according to claim 5, wherein the circuit and the storage media identifies the carrier.

7. The carrier identification system according to claim 6, wherein the identified carrier corresponds to the type of device-under-test.

8. The carrier identification system according to claim 7, wherein an IC testing controller checks if the devices-under-test output by the carrier identification system are in agreement with the devices-under-test detected in a currently operating test.

9. The carrier identification system according to claim 8, wherein said IC testing controller stops testing of the devices-under-test when the devices under test are not in agreement.

10. The carrier identification system according to claim 5, wherein the detected data signals comprise bits, each of the bits corresponding to one of the data through holes.

11. The carrier identification system according to claim 5, wherein the circuit comprises a latch circuit for storing each of the data signals.

12. The carrier identification system according to claim 5, wherein said timing detector and said data detector are secured to a fitting member having a U-shape with a lower side positioned below and an upper side positioned above a path in a direction of transfer for the carriers.

13. The carrier identification system according to claim 12, wherein said timing detector comprises a light emitting device secured to one of the upper side and the lower side of the fitting member and an optical receiver secured to the other of the upper side and the lower side of the fitting member, said light emitting device and said optical receiver being positioned to detect light passing through the timing through holes as the carrier is traveling along the path between the upper side and the lower side of the fitting member.

14. The carrier identification system according to claim 12, wherein said data detector comprises a light emitting device secured to one of the upper side and the lower side of the fitting member and an optical receiver secured to the other of the upper side and the lower side of the fitting member, said light emitting device and said optical receiver being positioned to detect light passing through the data through holes as the carrier is traveling along the path between the upper side and the lower side of the fitting member.

* * * * *